US010993476B2

(12) United States Patent
Guo

(10) Patent No.: US 10,993,476 B2
(45) Date of Patent: May 4, 2021

(54) ELECTRIC HEATER BASED ELECTRONIC SMOKING DEVICE

(71) Applicant: SHENZHEN YUKAN TECHNOLOGY CO., LTD, Guangdong (CN)

(72) Inventor: Hongli Guo, Guangdong (CN)

(73) Assignee: SHENZHEN YUKAN TECHNOLOGY CO., LTD, Guangdong (CN)

(*) Notice: Subject to any disclaimer, the term of this patent is extended or adjusted under 35 U.S.C. 154(b) by 308 days.

(21) Appl. No.: 16/006,896

(22) Filed: Jun. 13, 2018

(65) Prior Publication Data

US 2018/0289073 A1    Oct. 11, 2018

Related U.S. Application Data

(63) Continuation of application No. PCT/CN2017/102368, filed on Sep. 20, 2017.

(30) Foreign Application Priority Data

Oct. 28, 2016 (CN) .......... 201621196068.2
Nov. 28, 2016 (CN) .......... 201611067068.7

(51) Int. Cl.
A24F 13/00 (2006.01)
A24F 17/00 (2006.01)
(Continued)

(52) U.S. Cl.
CPC .......... *A24F 47/008* (2013.01); *A61M 11/042* (2014.02); *A61M 15/06* (2013.01);
(Continued)

(58) Field of Classification Search
CPC ........ A24F 47/008; A24F 40/46; A24F 40/57; A61M 11/042; A61M 15/06
(Continued)

(56) References Cited

U.S. PATENT DOCUMENTS 10,206,430 B2 * 2/2019 Mironov ................ A24B 15/16
10,492,533 B2 * 12/2019 Bernauer ............... A24F 40/40
(Continued)

FOREIGN PATENT DOCUMENTS

CN    1333657 A    1/2002
CN    1287699 C    12/2006
(Continued)

OTHER PUBLICATIONS

The Extended European search report issued in corresponding European application 17873061.0 dated Jun. 19, 2019.
(Continued)

*Primary Examiner* — Abdullah A Riyami
*Assistant Examiner* — Thang H Nguyen
(74) *Attorney, Agent, or Firm* — Fish IP Law, LLP

(57) ABSTRACT

The present invention discloses an electronic smoking device, comprising a power supply, a controller and a heater, wherein the heater is a cylindrical shape having in the middle a heating chamber into which a cigarette is inserted, and the heater comprises at least one heating unit comprising an electronic switch and an annular electric heating element; and the electric heating element is connected to the power supply by the electronic switch, and a control terminal of the electronic switch is connected to a control signal output terminal of the controller. In the present invention, tobacco in a cigarette is heated by an electric heater so that a smoker can just smoke nicotine produced by heating the tobacco. The electric heater will not produce naked flame and therefore the heated tobacco will not produce tar and carbon monoxide, so that the harm of the tobacco to the smoker can be reduced.

5 Claims, 2 Drawing Sheets

(51) Int. Cl.
    *A24F 25/00*      (2006.01)
    *A24F 47/00*      (2020.01)
    *H05B 1/02*       (2006.01)
    *A61M 11/04*      (2006.01)
    *A61M 15/06*      (2006.01)
    *H01C 7/00*       (2006.01)

(52) U.S. Cl.
    CPC ... *H05B 1/0291* (2013.01); *A61M 2205/3368* (2013.01); *H01C 7/008* (2013.01); *H05B 2203/019* (2013.01); *H05B 2203/02* (2013.01)

(58) Field of Classification Search
    USPC .......................................................... 131/329
    See application file for complete search history.

(56) References Cited

U.S. PATENT DOCUMENTS

| | | | | |
|---|---|---|---|---|
| 10,687,553 | B2* | 6/2020 | Kaufman | A61M 15/06 |
| 2016/0235122 | A1* | 8/2016 | Krietzman | A24B 15/16 |
| 2017/0311648 | A1* | 11/2017 | Gill | A24F 47/008 |
| 2018/0042306 | A1* | 2/2018 | Atkins | A24F 47/008 |
| 2018/0289073 | A1* | 10/2018 | Guo | A61M 11/042 |
| 2019/0045844 | A1* | 2/2019 | Reevell | H05B 1/0244 |
| 2019/0166918 | A1* | 6/2019 | Thorsen | A24F 40/50 |
| 2020/0093182 | A1* | 3/2020 | Monsalud | A61M 15/0003 |

FOREIGN PATENT DOCUMENTS

| | | | | |
|---|---|---|---|---|
| CN | 103653258 | A | 3/2014 | |
| CN | 103720048 | A | 4/2014 | |
| CN | 103734912 | A | 4/2014 | |
| CN | 103750566 | * | 4/2014 | ............ A24F 13/00 |
| CN | 103750566 | A | 4/2014 | |
| CN | 103815546 | A | 5/2014 | |
| CN | 203575658 | U | 5/2014 | |
| CN | 104770897 | A | 7/2015 | |
| CN | 205492626 | U | 8/2016 | |
| CN | 105996132 | A | 10/2016 | |
| CN | 106418724 | A | 2/2017 | |
| JP | 2016534730 | A | 11/2016 | |
| WO | 2014110119 | A1 | 7/2014 | |
| WO | 2015140312 | A1 | 9/2015 | |
| WO | 2016075436 | A1 | 5/2016 | |

OTHER PUBLICATIONS

International search report issued in corresponding international application No. PCT/CN2017/102368 dated Dec. 26, 2017.

* cited by examiner

ELECTRIC HEATER BASED ELECTRONIC SMOKING DEVICE

TECHNICAL FIELD

The present invention relates to a smoking set and in particular to an electronic smoking device.

BACKGROUND OF THE PRESENT INVENTION

Smoke of tobacco contains at least three chemical substances: tar, nicotine and carbon monoxide. Tar is a mixture of several substances and will be condensed into a viscous carcinogen in the lung. The boiling point of nicotine is 247° C., and nicotine is an addictive drug which is absorbed by the lung and mainly acts on the nervous system. Carbon monoxide is produced by incomplete combustion of tobacco, can reduce the ability of erythrocytes to transport oxygen to the whole body and is of great harm to the human body.

During smoking, except for the outer part of the cigarette, other parts are basically combusted in the case of insufficient oxygen and most of carcinogens such as tar are produced at 500° C. to 900° C. Tar and carbon monoxide which are produced during smoking enter the respiratory tract of smokers following the smoke flow and thus cause harm to the smokers.

SUMMARY OF THE PRESENT INVENTION

The technical problem to be solved by the present invention is to provide an electronic smoking device which will not produce tar and carbon monoxide during smoking.

To solve the technical problem, the electronic smoking device comprises a power supply, a controller and a heater, wherein the heater is a cylindrical shape having in the middle a heating chamber into which a cigarette is inserted, and the heater comprises at least one heating unit comprising an electronic switch and an annular electric heating element; and the electric heating element is connected to the power supply by the electronic switch, and a control terminal of the electronic switch is connected to a control signal output terminal of the controller.

In the electronic smoking device, the heating unit comprises a thermistor; after the electronic switch, the thermistor and the electric heating element are connected in series, one end of the formed circuit is connected to a positive pole of the power supply and the other end thereof is connected to a negative pole of the power supply; and the thermistor is arranged within an internal hole of the annular electric heating element.

The electronic smoking device comprises plural heating units and electric heating elements of the plural heating units are connected in series axially to form the cylindrical heater; and the control terminal of the electronic switch of each heating unit is connected to one control signal output terminal of the controller.

In the electronic smoking device, the electric heating element is an electric heating film or an electric heating wire.

The electronic smoking device has a cylindrical shell, the heater is arranged in a middle portion of an internal hole of the shell, the power supply is a battery arranged at a rear end of the shell, and there is a hand-holding portion at a front end of the shell.

The electronic smoking device comprises a circuit board on which the controller and the electronic switch are arranged, and the circuit board is arranged at the rear end of the shell.

In the electronic smoking device of the present invention, tobacco in a cigarette is heated by an electric heater so that a smoker can just smoke nicotine produced by heating the tobacco. The electric heater will not produce naked flame and therefore the heated tobacco will not produce tar and carbon monoxide, so that the harm of the tobacco to the smoker can be reduced.

BRIEF DESCRIPTION OF THE DRAWINGS

The present invention will be further described below in detail with reference to the accompanying drawings by specific implementations.

DETAILED DESCRIPTION OF THE PRESENT INVENTION

Figure 1:
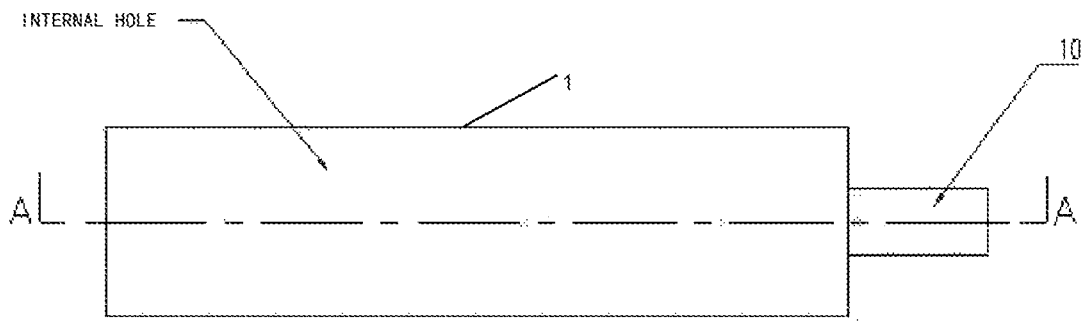
FIG. 1 is a front view of an electronic smoking device according to an embodiment of the present invention.
Figure 3:
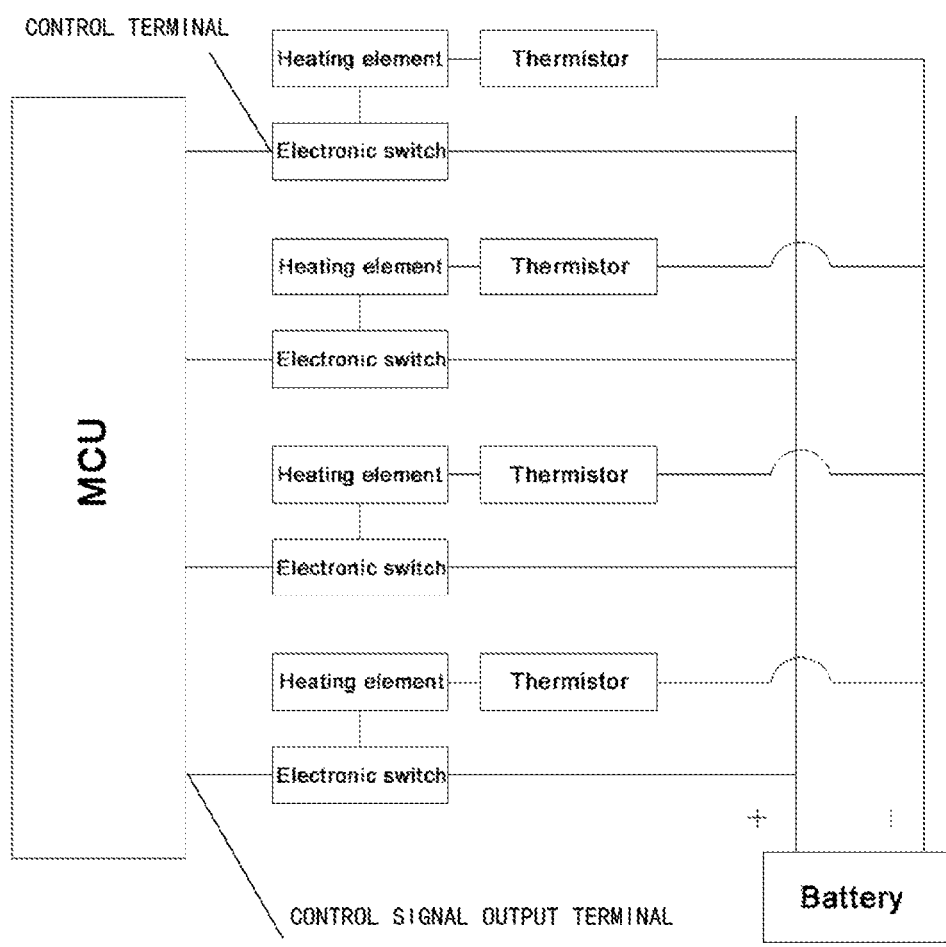
FIG. 3 is a circuit block diagram of the electronic smoking device according to an embodiment of the present invention.
Figure 2:
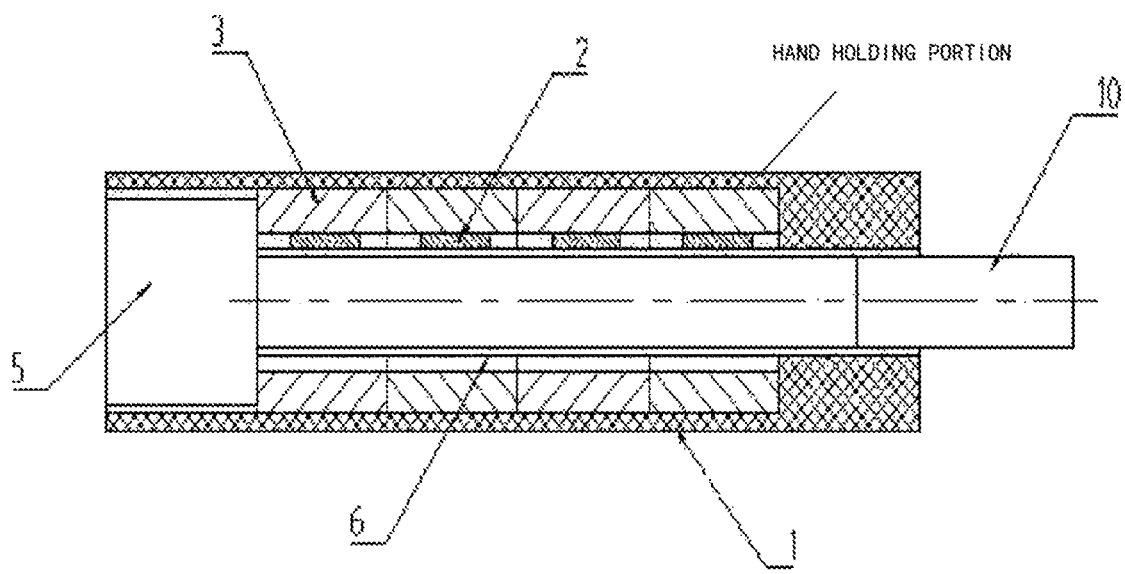
FIG. 2 is a sectional view of FIG. 1 in a direction A.

The structure of an electronic smoking device according to the embodiment of the present invention is as shown in FIG. 1 to FIG. 3, comprising a shell 1, a battery 5, a Microcontroller Unit (MCU) and a heater.

The heater comprises at least four heating units and each heating unit comprises an electronic switch, a thermistor 2 and an annular electric heating element 3. The electric heating element 3 can be an electric heating film or an electric heating wire. The thermistor 2 is arranged within an internal hole of the annular electric heating element 3.

Electric heating elements 3 of the four heating units are connected in series axially to form the cylindrical heater having in the middle a heating chamber 6 into which a cigarette 10 is inserted.

A control terminal of each electronic switch is respectively connected to a control signal output terminal of the MCU, and the electronic switch can be a triode or an MOS transistor.

After the electronic switch, the thermistor and the electric heating element are connected in series, one end of the formed circuit is connected to a positive pole of the battery 5 and the other end thereof is connected to a negative pole of the battery 5.

The shell 1 is a cylindrical shape. The heater is arranged in a middle portion of an internal hole of the shell 1, the battery 5 is arranged at a rear end of the shell 1, and there is a hand-holding portion at a front end of the shell 1.

The MCU and the electronic switch are arranged on a circuit board (not shown) which is arranged at the rear end of the shell 1.

When the electronic smoking device according to the embodiment of the present invention is used, the cigarette is inserted into the heating chamber of the cylindrical heater with the filter being left outside, and then the control circuit is started by the MCU. The MCU starts the electric heating elements one by one from left to right. The operating temperature of the electric heating elements is maintained at about 300° C., which doesn't reach the minimum temperature of 500° C. at which tar is produced. In this case, only nicotine is volatilized so that a smoker can smoke nicotine vapor. Since there is no naked flame, carbon monoxide will not be produced and the smoker will not smoke tar and carbon monoxide. Each electric heating element works for a period of time, and the next electric heating element on the right is started after nicotine of a cigarette section corresponding to this heating section is completely volatilized. When all heating sections finish working, the electronic smoking device is shut down and waits for the insertion of a new cigarette.

In the electronic smoking device according to the embodiment of the present invention, tobacco in a cigarette is heated by an electric heater so that a smoker can just smoke nicotine produced by heating the tobacco. The electric heater will not produce naked flame and therefore the heated tobacco will not produce tar and carbon monoxide, so that the harm of the tobacco to the smoker can be reduced.

What is claimed is:

1. An electronic smoking device, comprising a power supply, a controller, and a heater, wherein
    the heater comprises at least one heating unit, each of the at least one heating units comprising an electronic switch, an annular electric heating element connected to the electronic switch, and a thermistor connected to the annular electric heating element, the annular electric heating element defining an internal hole for receiving the thermistor,
    the annular electric heating element of each of the at least one heating units is connected directly in series along an axial direction to define a cylindrical shape having a mid-positioned heating chamber configured to receive a cigarette, the electronic switch disposed outside the heating chamber; and
    the electric heating element is connected to the power supply via the electronic switch, and a control terminal of the electronic switch is connected to a control signal output terminal of the controller to receive a control signal from the contoller, the control signal being used to control the electronic switch to be turned on or turned off to enable or disable the annular electric heating element.

2. The electronic smoking device according to claim 1, after the electronic switch, the thermistor and the electric heating element are connected in series to form a circuit, one end of the circuit thus formed is connected to a positive pole of the power supply and the other end thereof is connected to a negative pole of the power supply.

3. The electronic smoking device according to claim 1, wherein the electronic smoking device comprises plural heating units and electric heating elements of the plural heating units are connected in series axially to form the cylindrical heater; and the control terminal of the electronic switch of each heating unit is connected to one control signal output terminal of the controller.

4. The electronic smoking device according to claim 1, wherein the electric heating element is an electric heating film or an electric heating wire.

5. The electronic smoking device according to claim 2, wherein the electronic smoking device has a cylindrical shell, the heater is arranged in a middle portion of an internal hole of the shell, the power supply is a battery arranged at a rear end of the shell, and there is a hand-holding portion at a front end of the shell.

* * * * *